US008828437B2

(12) United States Patent
Sundberg et al.

(10) Patent No.: US 8,828,437 B2
(45) Date of Patent: *Sep. 9, 2014

(54) THERMOGELLING ANAESTHETIC COMPOSITIONS

(71) Applicant: Pharmanest AB, Solna (SE)

(72) Inventors: Mark Sundberg, Arsta (SE); Arne Brodin, Sodertalje (SE); Nils Kallberg, Taby (SE)

(73) Assignee: Pharmanest AB, Solna (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/172,794

(22) Filed: Feb. 4, 2014

(65) Prior Publication Data

US 2014/0155434 A1 Jun. 5, 2014

Related U.S. Application Data

(63) Continuation of application No. 13/638,511, filed as application No. PCT/EP2011/055009 on Mar. 31, 2011.

(60) Provisional application No. 61/325,418, filed on Apr. 19, 2010.

(30) Foreign Application Priority Data

Apr. 1, 2010 (SE) .................................... 1050321

(51) Int. Cl.
*A61K 8/00* (2006.01)
*A61K 47/44* (2006.01)
*A61K 9/00* (2006.01)
*A61K 47/34* (2006.01)

(52) U.S. Cl.
CPC ............... *A61K 9/0034* (2013.01); *A61K 47/44* (2013.01); *A61K 47/34* (2013.01); *A61K 9/0019* (2013.01)

USPC .......................................................... 424/484

(58) Field of Classification Search
None
See application file for complete search history.

(56) References Cited

U.S. PATENT DOCUMENTS

| 8,663,688 B2 * | 3/2014 | Fernandez et al. ............ 424/487 |
| 2004/0220283 A1 | 11/2004 | Zhang et al. |
| 2005/0027019 A1 | 2/2005 | Zhang et al. |
| 2007/0298005 A1 | 12/2007 | Thibault |
| 2008/0154210 A1 | 6/2008 | Jordan et al. |
| 2012/0294907 A1 | 11/2012 | Zhang et al. |

FOREIGN PATENT DOCUMENTS

| AU | 2006201233 B2 | 10/2007 |
| EP | 0517160 A1 | 12/1992 |
| EP | 1629852 A2 | 3/2006 |
| KR | 20020013248 A | 2/2002 |

(Continued)

OTHER PUBLICATIONS

Written Opinion, Intellectual Property Office of Singapore, from the corresponding Singapore Application No. 201206824-3, Jul. 19, 2013.
Notification of First Office Action, China Intellectual Property Office, from the corresponding Chinese Application No. 201180016573.8, Aug. 1, 2013.

(Continued)

*Primary Examiner* — Anand Desai
*Assistant Examiner* — Melissa Mercier
(74) *Attorney, Agent, or Firm* — LeClairRyan, a Professional Corporation

(57) ABSTRACT

The present invention relates to a thermogelling pharmaceutical composition comprising local anaesthetics in base form and which is suitable for topical administration. The compositions further comprise a polyoxyethylene castor oil and one or more surfactants to obtain thermogelling characteristics.

28 Claims, 1 Drawing Sheet

(56) References Cited

FOREIGN PATENT DOCUMENTS

| | | | |
|---|---|---|---|
| WO | 97/38675 | A1 | 10/1997 |
| WO | 01/22907 | A1 | 4/2001 |
| WO | 03/017976 | A1 | 3/2003 |
| WO | 03/017977 | A1 | 3/2003 |
| WO | 2004/076561 | A1 | 9/2004 |
| WO | 2004076561 | A1 * | 9/2004 |
| WO | 2008/015190 | A2 | 2/2008 |

OTHER PUBLICATIONS

International Search Report from corresponding PCT Application PCT/EP2011/055009, (2011).

International-type Search Report for Patent Application No. SE 1050321-7 (mailed Jan. 16, 2011).

Jones et al., "Solute and Solvent Effects on the Thermorheological Properties of Poly(oxyethylene)-Poly(oxypropylene) Block Copolymers: Implications for Pharmaceutical Dosage Form Design," J. App. Poly. Sci. 87:1016-1026 (2003).

* cited by examiner

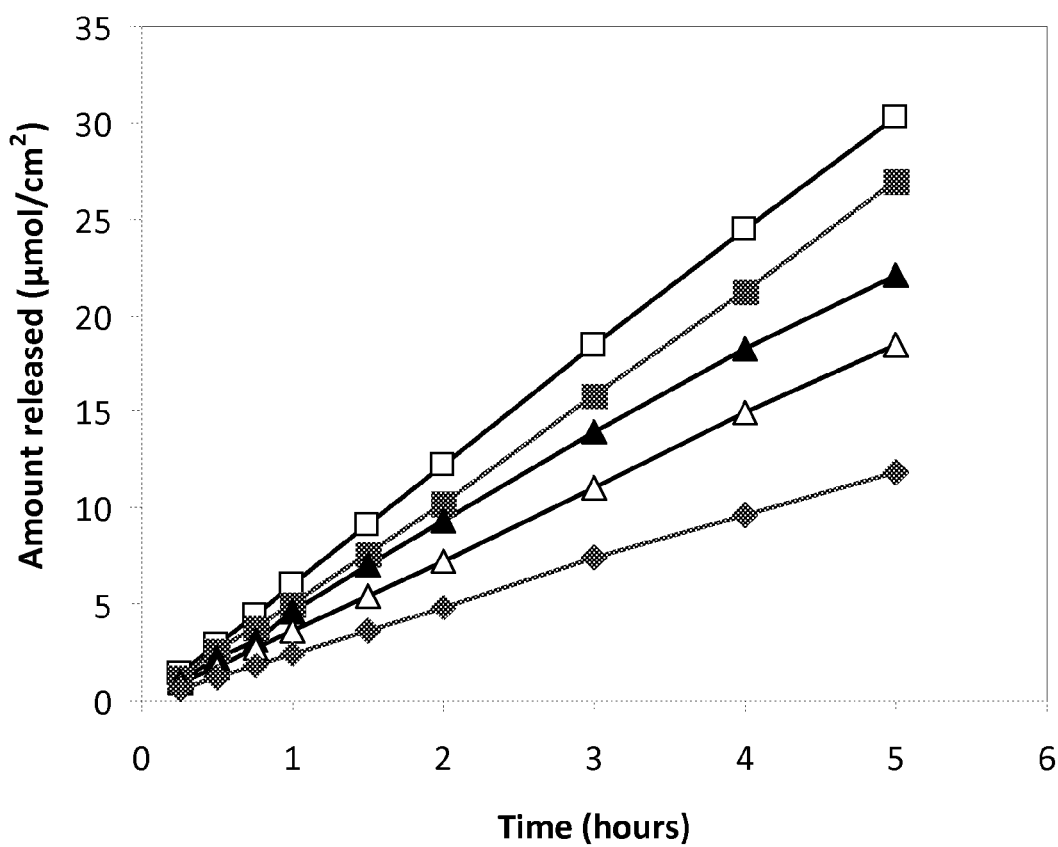

THERMOGELLING ANAESTHETIC COMPOSITIONS

This application is a continuation of U.S. patent application Ser. No. 13/638,511, which is a national stage application under 35 U.S.C. §371 of PCT/EP2011/055009 filed Mar. 31, 2011, and claims priority under 35 U.S.C. §119 of U.S. Provisional Patent Application Ser. No. 61/325,418 filed Apr. 19, 2010, and Sweden Patent Application 1050321-7 filed Apr. 1, 2010.

FIELD OF THE INVENTION

The present invention relates to new pharmaceutical compositions comprising local anaesthetics for topical administration. The compositions can be used for reducing pain in connection with clinical conditions and clinical procedures.

BACKGROUND TO THE INVENTION

Local anaesthetics are commonly used to inhibit nociceptive pain, and are usually administered by local injection. Pharmaceutical compositions for local injection normally contain local anaesthetics at a concentration of 1 to 2%.

In the preparation of pharmaceutical compositions for topical administration it is preferred to have the local anaesthetic present at a higher concentration.

Local anaesthetics of the amide type, ATC code N01BB, are weak bases with a $pK_a$ of around 8. Consequently, in an aqueous solution at neutral pH these local anaesthetics are mostly present in their acid form. However, the acid form is charged and therefore less suitable to pass through biological membranes. In pharmaceutical compositions for topical administration it is therefore preferred to have the local anaesthetic present in its base form which can readily pass through biological membranes. This can be achieved by adjusting the pH of the pharmaceutical compositions to a pH around or even preferably above the $pK_a$ of the local anaesthetic, i.e. to a pH above 8 or higher.

However, this leads to problems of the base form of the local anaesthetics relating to poor solubility and stability in aqueous solutions.

This problem has been addressed for e.g. in EP 0833612 which discloses a pharmaceutical composition comprising an eutectic mixture of lidocaine base and prilocaine base. This mixture is in oil form at room temperature and can therefore be formulated as an emulsion. This eutectic mixture can only be obtained with a few local anaesthetic mixtures with suitable melting points, exemplified by lidocaine base and prilocaine base.

EP 1629852 describes a system where the local anaesthetic is kept in a solution at acidic pH and only mixed with a buffering solution with high pH shortly prior to use, providing a solution of the local anaesthetic at a pH between 5.5 and 7. In this pH interval only a small portion of the local anaesthetic is present in the base form, the form that readily penetrates membranes.

Despite many efforts of developing effective topical compositions of local anaesthetic agents, there still is need for a composition that safely and effectively can exert an anaesthetic effect at sites inside the body while meeting requirements of stability, sterility and a compliant administration procedure. For this purpose, the present inventors studied different thermogelling agents together with local anaesthetics of the amide type at a basic pH. The results indicated difficulties to find stability and to settle stable conditions even with suitable candidates of such thermogelling agents. The present invention aims at providing such stable sterilizable thermogelling pharmaceutical compositions comprising one or more local anaesthetics and at a concentration sufficiently high and at a sufficiently high pH to be able to provide effective pain relief following topical administration, while being easy to administer with conventional tools and sufficiently cohesive at the administration site to exert the anaesthetic effect in a safe, controlled and predetermined manner.

DESCRIPTION OF THE INVENTION

Before the present invention is described, it is to be understood that the terminology employed herein is used for the purpose of describing particular embodiments only and is not intended to be limiting, since the scope of the present invention will be limited only by the appended claims and equivalents thereof.

It must be noted that, as used in this specification and the appended claims, the singular forms "a," "an," and "the" include plural referents unless the context clearly dictates otherwise.

Also, the term "about" is used to indicate a deviation of +/−2% of the given value, preferably +/−5%, and most preferably +/−10% of the numeric values, where applicable.

In a general embodiment, the present invention relates to a stabilized thermogelling pharmaceutical composition comprising an anaesthetically effective amount of one or more local anaesthetics; a polyoxyethylene castor oil in an amount of between about 10 and about 30% by weight; and one or more surfactants in an amount of at least 15% by weight to provide the composition with thermogelling properties.

In the context of this specification, the term "surfactant" refers to any agent that acts as an emulsifier and/or suspension stabilizer and/or as a thickening agent, preferably with thermogelling properties most preferably with thermoreversible gelling properties. If only one surfactant is used in the composition, it must be selected with care and in suitable amounts so that it acts both as an emulsifier, as well as a thickening agent, preferably with thermoreversible gelling properties.

In the context of the present composition, "thermogelling" has the meaning that the compositions are generally liquid with low viscosity at room (ambient) temperature of at about 20 to 25° C., but is a gel at body temperature at about 37 to 40° C. The transition between liquid and gel does not necessarily need to be at body temperature, but preferably the composition shall undergo transition in the interval about 30 to about 37° C. It is, however, important that the transition is sufficiently distinct at a defined temperature or at a fairly narrow temperature interval.

The thermogelling compositions generally are possible to eject from standard cannulas or other injection devices in preferred embodiments with a needle/tip as fine as having an inner diameter of about 1 mm, such as about 0.5 to about 2 mm at room temperature, while the compositions from a cohesive viscous gel at body temperature. Many materials with thermogelling characteristics are well known for topical drug delivery, such as different celluloses and surface active block copolymers. In the context of the present invention, it is suitable that the compositions have an elasticity modulus (G') at room temperature of below about 20 Pa, more suitable about 1 Pa and in certain embodiments as low as 0.001 to 0.1 Pa, while the elasticity modulus at body temperature in within the approximate range of 50 to 10000 Pa, such as about $10^4$ Pa at body temperature. Suitably, the viscosity at room temperature is preferably less than about 20 Pas, more preferably from about 0.4 to about 10 Pas, preferably less than about 20 Pas. Inventive compositions including thermogelling components suitable to meet such requirements are embodied in the following sections. Thermoreversible has the meaning that the rheological characteristics should be possible to repeat after warming and cooling the compositions.

"Stabilized" in the meaning of the present invention indicates that the compositions does not precipitate, degrade or in other terms change their appearance or usefulness during storage and/or heat sterilization including their thermogelling and preferably thermoreversible gelling properties.

Preferably, the pharmaceutical composition of the invention further comprises a solubilizer in an amount of between about 0 and about 10% by weight, more preferably in an amount of between 1 and 5% by weight.

The Pharmaceutical composition comprises local anaesthetics present in an amount of between 1 and 10% by weight, preferably in an amount of between 1 and 7% by weight. Most suitable concentrations to include depend on the solubility limits achievable with the inventive composition systems. Finding such effective concentrations is within the general knowledge of the experienced with formulating local anaesthetics.

An important feature of the present invention is the final pH-value of the pharmaceutical compositions which is adjusted to a value where sufficient amounts of the local anaesthetic(s) are present in the uncharged base form. This feature is important to promote the penetration of the local anaesthetic into the tissue and consequently be able to exert the anaesthetic effect. That the pH is high enough so that a sufficient amount of the local anaesthetic is in its base form (close to or higher than the $pK_a$ of the local anaesthetics) is an advantage over a physiological pH (7.4) due to the promoted penetration of the uncharged base form.

Accordingly, the pH-value of the pharmaceutical composition is adjusted with suitable acid or base in such a way that the final pH-value for the composition is higher or equal to the $pK_a$ of the local anaesthetic minus 1.0, preferably the final pH-value for the composition is higher or equal to the $pK_a$ of the local anaesthetic minus 0.5, even more preferably the final pH-value for the composition is higher or equal to the $pK_a$ of the local anaesthetic.

If the pharmaceutical composition comprises two or more local anaesthetics the final pH-value for the composition is adjusted in relation to the $pK_a$ of the local anaesthetic with the lowest $pK_a$ value.

TABLE 1

Examples of $pK_a$ for local anaesthetics

| Local anaesthetic | $pK_a$ |
|---|---|
| lidocaine | 7.9 |
| prilocaine | 7.9 |
| mepivacaine | 7.6 |
| ropivacaine | 8.1 |
| bupivacaine | 8.1 |
| levobupivacaine | 8.1 |

Preferably, the pharmaceutical compositions of the invention include the base form of one or more local anaesthetics of the amide type ATC code N01BB and have a pH of at least 8.0, Suitable such local anaesthetics of the amide type is selected from the group consisting of lidocaine, prilocaine, mepivacaine, ropivacaine, bupivacaine, and levobupivacaine. In a particular embodiment the local anaesthetic is the base form of lidocaine present in an amount of 1 to 7% by weight, preferably from 2 to 6% by weight.

The polyoxyethylene castor oil acting as a primary solubilizer is present in an amount of between 10 and 30% by weight, preferably the polyoxyethylene castor oil is selected from polyoxyethylene 35 castor oils, and most preferably the polyoxyethylene castor oil is Cremophor EL.

Polyoxyethylene castor oil derivatives are a series of materials obtained by reacting varying amounts of ethylene oxide with either castor oil or hydrogenated castor oil. Several different types of material are commercially available, the best-known being the Cremophor series (BASF Corp). Polyoxyethylene castor oil derivatives are complex mixtures of various hydrophobic and hydrophilic components. Members within each range have different degrees of ethoxylation (moles)/PEG units as indicated by their numerical suffix (n). The chemical structures of the polyethoxylated hydrogenated castor oils are analogous to polyethoxylated castor oils with the exception that the double bond in the fatty chain has been saturated by hydrogenation. The PhEur 2005 states that polyoxyl castor oil contains mainly ricinoleyl glycerol ethoxylated with 30-50 molecules of ethylene oxide with small amounts of macrogol ricinoleate, and of the corresponding free glycols. The PhEur 2005 also states that polyoxyl hydrogenated castor oil contains mainly trihydroxystearyl glycerol ethoxylated with 7-60 molecules of ethylene oxide. In polyoxyl 35 castor oil (Cremophor EL) the relatively hydrophobic constituents comprise about 83% of the total mixture, the main component being glycerol polyethylene glycol ricinoleate. Other hydrophobic constituents include fatty acid esters of polyethylene glycol along with some unchanged castor oil. The hydrophilic part (17%) consists of polyethylene glycols and glycerol ethoxylates. Cremophor ELP, a purified grade of Cremophor EL is also a polyoxyl 35 castor oil, it has a lower content of water, potassium, and free fatty acids and hence is claimed to have improved stability.

Synonyms applicable to polyoxyethylene castor oil derivatives are shown below in Table 2.

TABLE 2

Synonyms of selected polyoxyethylene castor oil derivatives

| Name | Synonym |
|---|---|
| Polyoxyl 5 castor oil | Acconon CA-5; castor oil POE-5; Etocas 5; Hetoxide C-5; Jeechem CA-5; PEG-5 castor oil; polyoxyethylene 5 castor oil. |
| Polyoxyl 9 castor oil | Acconon CA-9; castor oil POE-9; Jeechem CA 9; PEG-9 castor oil; polyoxyethylene 9 castor oil; Protachem C-A9. |
| Polyoxyl 15 castor oil | Acconon CA-15; castor oil POE-15; Jeechem CA15; PEG-15 castor oil; polyoxyethylene 15 castor oil; Protachem CA-15. |
| Polyoxyl 35 castor oil | Castor oil POE-35; Cremophor EL; Cremophor ELP; Etocas 35; glycerol polyethyleneglycol ricinoleate; PEG-35 castor oil; polyethoxylated castor oil; polyoxyethylene 35 castor oil. |
| Polyoxyl 40 castor oil | Castor oil POE-40; Cirrasol G-1284; Croduret 40; Etocas 40; Eumulgin RO; Hetoxide C40; Jeechem CA-40; Marlowet R40; Niccol CO 40TX; Nonionic GR-40; PEG-40 castor oil; polyoxyethylene 40 castor oil; Protachem CA40. |
| Polyoxyl 40 hydrogenated castor oil | Cremophor RH 40; Croduret 40; Eumulgin HRE 40; glycerol polyethyleneglycol oxystearale; Hetoxide HC40; hydrogenated castor oil POE-40; Jeechem CAH-40; PEG-40 hydrogenated castor oil; polyethoxylated hydrogenated castor oil; polyoxyethylene 40 hydrogenated castor oil; Lipocol HC0 40; Lipocol LAV HCO 40; Nikkol HCO 40 Pharma; Nonionic GRH-40; Protachem CAH-40. |
| Polyoxyl 60 castor oil | Castor oil POE-60; Jeechem CA-60; Nikkol CO 60TX; PEG-60 castor oil; polyoxyethylene 60 castor oil. |

TABLE 2-continued

Synonyms of selected polyoxyethylene castor oil derivatives

| Name | Synonym |
|---|---|
| Polyoxyl 60 hydrogenated castor oil | Croduret 60; Eumulgin HRE 60; Hetoxide HC60; hydrogenated castor oil POE-60; Jeechem CAH-60; PEG-60 hydrogenated castor oil; polyoxyethylene 60 hydrogenated castor oil; Lipocol HCO 60; Nikkol HCO 60 Pharma; Protachem CAH-60 |
| Polyoxyl 100 castor oil | Hydrogenated castor oil POE-100; Jeechem CA-100; PEG-100 hydrogenated castor oil; polyoxyethylene 100 hydrogenated castor oil. |
| Polyoxyl 100 hydrogenated castor oil | Cirrasol G-1300; Jeechem CA-100; Nikkol HCO 100; polyoxyethylene 100 hydrogenated castor oil. |
| Polyoxyl 200 castor oil | Hetoxide C200; Jeechem CA-200; polyoxyethylene 200 castor oil; PEG-200 castor oil; castor oil POE-200. |
| Polyoxyl 200 hydrogenated castor oil | Hydrogenated castor oil POE-200; Jeechem CAH-200; PEG-200 hydrogenated castor oil; polyoxyethylene 200 hydrogenated castor oil. |

The surfactant can be a non-ionic or ionic surfactant, preferably the surfactant is a non-ionic surfactant present in amount of about 15 to about 25% by weight and in certain embodiments between about 18 to 22% by weight. It is possible to use at least one surfactant having thermoreversible gelling properties. By choosing surfactant(s) with hydrophobic and hydrophilic domains in appropriate amounts, it is possible to obtain pharmaceutical compositions with local anaesthetics with thermoreversible gelling properties. This enables the pharmaceutical composition to be less viscous at room temperature and when applied at the targeted site the viscosity of the composition is increased. Thereby, the composition can safely remain at site where it is administered and deliver the active ingredient in a controlled manner. Preferably the surfactants with thermoreversible gelling properties are non-ionic block copolymers of polyoxy(ethylene) and poly(oxyproylene) conforming to the general formula HO—$[C_2H_4O]_\alpha$—$[C_3H_6O]_\beta$—$[C_2H_4O]_\alpha$—H, $\alpha$ and $\beta$ representing the number of hydrophilic ethylene oxide and hydrophobic propylene oxide chains respectively. They are generally referred to as poloxamers.

According what is the preferable with the present invention, the pharmaceutical compositions comprise non-ionic block copolymers of the poly(oxyethylene) and poly(oxypropylene) type present in an amount of at least 15% by weight, preferably from about 18 to about 25% by weight, exemplified by 20 to 22% by weight. Especially suitable variants of such block copolymers comprise a higher molecular weight poloxamer and a lower molecular weight poloxamer, and wherein the higher molecular weight poloxamer is present in excess to the lower molecular weight poloxamer. Typically the poloxamers comprise a mixture of poloxamer 188 and poloxamer 407, suitably the two poloxamer are present in equal amounts or close to equal amounts. In a special embodiment the weight ratio of poloxamer 407 to poloxamer 188 is from about 1.5 to about 1.3.

The additional solubilizer of the inventive compositions preferably is selected from the group consisting of suitable lower alcohols such as ethanol, propanol, isopropanol, propylene glycol and benzyl alcohol; glycerol formal, glycofural, polysorbates such as polysorbate 80 and ethyl acetate. Most preferably, the solubilizer is selected among ethanol and benzylalcohol.

The pharmaceutical compositions of the present invention further comprise water adding up to 100% by weight.

Certain preferred embodiments of the invention are pharmaceutical compositions comprise a local anaesthetic selected from lidocaine and prilocaine in an amount of between 2 to 6% by weight; a polyoxyethylene castor oil in an amount of between 15 to 30% by weight; one or more block copolymers of ethylene oxide and propylene oxide in an amount of between 15 to 30% by weight; and benzyl alcohol in an amount of between 0 to 2% by weight.

Other preferred embodiments of the inventive pharmaceutical comprise a local anaesthetic selected from lidocaine and prilocaine in an amount of between 2 to 6% by weight; a polyoxyethylene castor oil in an amount of between 10 to 30% by weight; one or more block copolymers of ethylene oxide and propylene oxide in an amount of between 20 to 30% by weight; and ethanol in an amount of between 2 to 5% by weight.

Still other embodiments comprise 2 to 6% by weight of lidocaine in base form; about 20 to 30% by weight of a polyoxyethylene castor oil; about 15 to 25% by weight of poloxamers; and no cosolubilzer.

Special embodiments of the composition according to the present invention comprise about 2 to 6% by weight of lidocaine in base form; about 10 to 30% by weight of a polyoxyethylene castor oil; about 15 to 25% by weight of poloxamers; about 1 to 5% by weigh of ethanol as cosolubilizer; and are adjusted to a pH-value of about 8.0 to 8.5. These embodiments are further exemplified with composition comprising about 4% lidocaine in base form; about 20 to 30% by weight of a polyoxyethylene castor oil; about 20 to 25% by weight of poloxamers; about 2 to 4% by weigh of ethanol as cosolubilizer adjusted to a pH-value of about 8.0 to 8.5.

In these preferred embodiments the polyoxyethylene castor oil is selected from polyoxyethylene 35 castor oils, preferable Chremophor EL and the poloxamers are selected among poloxamer 188 and 407 according to embodiments disclosed in the earlier general context.

Also in these embodiments the compositions have pH of about 8.0 to 8.5

The pharmaceutical composition according to the invention can be formulated for topical administration on any mucosal tissue, such as but not limited to, oral, nasal, ocular, intravaginal, intracervical, pericervical, intrauteral, intrarectal administration.

The pharmaceutical composition according to the invention can be formulated for dermal administration on healthy, diseased and/or injured skin. Dermal administration can be made directly from the container, by hand, or by means of or together with patches, bandages and wound dressings.

The pharmaceutical composition can be administrated by means of a syringe. The syringe can be further provided with an applicator. The applicator can be in the form of a tube.

The pharmaceutical compositions according to the present invention can be used for reducing pain in connection with various clinical conditions and clinical procedures.

Accordingly, in one aspect the present invention provides methods for reducing pain in connection with clinical conditions and clinical procedures comprising the administration of a pharmaceutical composition according to the invention.

Such clinical conditions are exemplified by, but not limited to, wound healing, especially burn wounds, skin ulcers, hemorrhoids, anal fissures, herpes zoster, herpes simplex infections, especially, herpes labialis, and herpes genitalis.

Such clinical procedures are exemplified by, but not limited to, obstetric procedures, such as during labor, gynaecological procedures, such as, abortions and application of intra uterine devices (IUD), hysteroscopy, in vitro fertilization, spontaneous and legal abortions, and general vaginal examination, dental procedures, surgical procedures, such as skin grafting.

Administration of the pharmaceutical composition on any mucosal tissue is possible, such as but not limited to, oral, nasal, intravaginal, intracervical, pericervical, intrauteral, intrarectal administration.

The pharmaceutical composition can also be dermally administered on healthy, diseased and/or injured skin. Dermal administration can be made directly from the container, by hand, or by means of or together with patches, bandages and wound dressings.

The administration can be made by means of a syringe. The syringe can be further provided with an applicator. The applicator can be in the form of a tube.

According to another aspect the invention relates to a method of manufacturing a local anaesthetics product comprising the steps of providing a composition of a local anaesthetic of the amide type in a concentration of between 1 to 10% by weight and solubilized with at least 10% by weight of a polyoxyethylene castor oil and an additional solubilizer in amount of 0 to 5% by weight. The composition further comprises at one or more surfactants in an amount of between of at least 15% by weight to provide the composition with thermo-reversible gelling properties. According to the method, a sealed container is prepared which comprises the composition. The method further comprises the step of subjecting the container with the composition to heat sterilization (autoclavation) below 120° C., preferably between about 110 to 120° C. and a period of about 10 minutes, preferably at about 115° C. for about 10 minutes. By the method a stable product with maintained thermo-reversible gel-forming and with so low level of viable microorganisms is obtain so that the product is suitable for topical administration to an internal body site. Any of the earlier disclosed compositions can be employed with this production method. It is of considerable advantage that the compositions of the present invention can be sterilized to an acceptable product at less harsh conditions than at autoclavation at 121° C. during 15 minutes, as otherwise expected/required by clinical authorities as it significantly reduces the risk for potentially harmful degradation products. It is contemplated that the systems components may synergistically contribute to an antimicrobial effect under the conditions of the method.

The compositions of the present invention so far generally disclosed and exemplified in the following section provide solutions to a number of technical problems. At first they admit sufficiently high amount of the local anaesthetic in its most effective form which necessitates a comparatively high presence of a solubilising agent that has been inventively selected as a polyoxyethylene castor oil present in at least about 10% by weight in the composition and an additional solubilizer such as ethanol. These components require a careful mutual adaptation to the agents for generating the thermoreversible gelling of the compositions, so they retain suitable rheological characteristics and sufficient stability from precipitation and other degrading effects both during storage and following heat sterilization.

In summary, the inventive composition surprisingly well meet the difficult requirements of a high, controlled anaesthetic effect at site inside the body, excellent compliance when administer and suitable stability also after final heat sterilization and storage.

DESCRIPTION OF THE FIGURE

FIG. 1 is a graph illustrating in-vitro release of local anaesthetics from pharmaceutical compositions. -□- 5% prilocaine HCl in 20% Chremophor, 1% benzyl alcohol; -■- 5% lidocaine in 23% Chremophor, 1% benzyl alcohol; -▲- 4% lidocaine in 23% Chremophor, 1% benzyl alcohol; -Δ- 3% lidocaine in 23% Chremophor, 1% benzyl alcohol; -♦- 2% lidocaine in 23% Chremophor, 1% benzyl alcohol.

EXAMPLES

Materials

Lidocaine (base form)—Apoteket Produktion & Laboratorier (Eur. Kval. E.)
Prilocaine HCl—Ph Eur
Chremophor EL—BASF (technical grade)
Poloxamer 188—BASF (technical grade)
Poloxamer 407—BASF (technical grade)
Benzyl alcohol—Ph Eur Example 1

Preparation of Lidocaine Compositions

Pharmaceutical compositions comprising the components according to Table 3 were prepared as described below.

Step 1. Component I is dissolved in II or, in applicable cases, in II and III under gentle warming.
Step 2. Components IV and V are dissolved in VI over night in a refrigerator, resulting into a clear slightly viscous solution.
Step 3. The solution from step 2 is put to the solution from step 1 followed by a thorough mixing, resulting into an opalescent thick gel. The gel can be made slightly thinner with an appropriate amount of VI, which is compensated with a reduction of the amount VIII.
Step 4. The pH of the gel is adjusted to 8 with VII.
Step 5. Remaining amount of VIII is put to the mixture from step 4 in order to reach the final amount of preparation.

TABLE 3

Formulations of lidocaine

| Components | | 1 | 2 | 3 | 4 | 5 | |
|---|---|---|---|---|---|---|---|
| I | Lidocaine | 5.00 | 5.00 | 5.00 | 5.00 | 5.00 | g |
| II | Cremophor EL | 20.00 | 23.00 | 23.00 | 25.00 | 27.00 | g |
| III | Benzyl alcohol | 1.00 | 1.00 | 2.00 | 0.00 | 0.00 | g |
| IV | Poloxamer 188 | 11.00 | 11.00 | 11.00 | 11.00 | 11.00 | g |
| V | Poloxamer 407 | 10.00 | 10.00 | 10.00 | 10.00 | 10.00 | g |
| VI | Purified water | 40.00 | 40.00 | 40.00 | 40.00 | 40.00 | g |
| VII | Hydrochloric acid 1M to pH 8 (approximately) | 1.60 | 1.60 | 1.60 | 1.60 | 1.60 | g |
| VIII | Purified water (approximately) | 11.40 | 8.40 | 7.40 | 7.40 | 5.40 | g |
| | Total | 100.00 | 100.00 | 100.00 | 100.00 | 100.00 | g |

The formulations all have thermoreversible gelling properties as a result of the presence of the poloxamers. When stored at room temperature no precipitation of the lidocaine was observed at the desired pH of 8 where lidocaine is mainly present in its active base form.

Example 2

Preparation of a Prilocaine Formulation

A pharmaceutical composition comprising the components according to Table 4 was prepared as described below.

Step 1. Components I and II are dissolved in III over night in a refrigerator, resulting in a clear slightly viscous solution.
Step 2. Component IV is dissolved in the solution from step 1.
Step 3. Components V and VI are added to the solution from step 2 followed by a thorough mixing, resulting in an opalescent mixture.
Step 4. The pH of the composition is adjusted to 8 with VII.

TABLE 4

| | Prilocaine formulation | |
|---|---|---|
| | Components | % (w/w) |
| I | Poloxamer 188 | 9.5 |
| II | Poloxamer 407 | 8.6 |
| III | Water | 34.5 |
| IV | Prilocaine HCl | 5.0 |
| V | Benzyl alcohol | 0.9 |
| VI | Cremophor EL | 19.9 |
| VII | NaOH 1M | 17.3 |

The formulation has thermoreversible gelling properties as a result of the presence of the poloxamers. No precipitation of the prilocaine was observed at the desired pH of 8 where prilocaine is mainly present in its active base form.

Example 3

In-Vitro Release of Local Anaesthetics from Pharmaceutical Compositions

Release of lidocaine and prilocaine from pharmaceutical compositions prepared according to Example 1 and Example 2 were measured overtime.

Results are presented in FIG. 1. A steady release of local anaesthetic could be observed from the different pharmaceutical preparations. The rate of release was related to the concentration of the local anaesthetic.

Although particular embodiments have been disclosed herein in detail, this has been done by way of example for purposes of illustration only, and is not intended to be limiting with respect to the scope of the appended claims that follow. In particular, it is contemplated by the inventor that various substitutions, alterations, and modifications may be made to the invention without departing from the spirit and scope of the invention as defined by the claims.

Example 4

Lidocaine Compositions with 40 mg/g and Different Amounts of Poloxamers and Cosolvents Pharmaceutical compositions comprising the components according to Table 5 were prepared as described below Version 1:
1. Mixing of Poloxamer 188 and Poloxamer 407 in Milli-Q water and simultaneously cooling the solution to speed up the dissolution.
2. Cremophor EL, lidocaine and ethanol are mixed separately by heating to 55° C. The solution is cooled down to room temperature.
3. Solution in (1) and (2) are mixed together (centrifugation 2000 rpm, max 30 minutes).
4. pH is measured in the total solution and pH is adjusted to pH 8.0-8.3 with 0.2-1.0 M HCl if necessary.

Version 2:
1. Mixing of Poloxamer 188 and Poloxamer 407 in Milli-Q Water and simultaneously cooling the solution to speed up the dissolution.
2. Cremophor EL, lidocaine and ethanol are mixed separately by heating to 55° C. The solution is cooled down to room temperature.
3. Solution in (1) and (2) are mixed together.
4. pH is measured in the total solution. pH is adjusted with 1 M NaOH or HCl to reach pH 8.0-8.3

The rheology of the prepared compositions was tested by dynamic oscillation and viscosity measurements. A TA Instruments AR-2000 was used at the following conditions:
Oscillation mode (oscillation stress 25 Pa)
Acrylic cone 4 cm, 1°, 27 μm gap
T=15-40° C.
Temperature increment=2° C./min
Frequency=1 Hz
Conditioning: 2 minutes before each measurement and 20 sec after each measurement

TABLE 5

Lidocaine formulations with 40 mg/g lidocaine and pH is adjusted with 1M HCl. The samples are not autoclaved.

| Poloxamers 188/407 (mg/g) | Cremophor EL (mg/g) | Co-solvent (mg/g) | pH | HCl tot (M) | Viscosity at 20° C. (Pa·s) | Rheology (dynamic oscillation) | Comments |
|---|---|---|---|---|---|---|---|
| 120/90 | 210 | 20 Ethanol | 8.08 | 0.02 | 5.9 | $T_{gel}$ = 24° C. $G'(25°\ C.)$ = 0.5 Pa, $G'(37°\ C.)$ = 40 Pa | No precipitation at 4° C., solid gel at 50° C. |
| 120/90 | 230 | 20 Ethanol | 8.04 | 0.02 | 8.4 | $T_{gel}$ = 25° C. $G'(25°\ C.)$ = 0.001 Pa, $G'(37°\ C.)$ = $10^4$ Pa | No precipitation at 4° C., solid gel at 50° C. |
| 120/90 | 250 | 20 Ethanol | 8.08 | 0.02 | 13.2 | $T_{gel}$ = 31° C. $G'(25°\ C.)$ = 3 Pa, $G'(37°\ C.)$ = | No precipitation at 4° C., solid |

TABLE 5-continued

Lidocaine formulations with 40 mg/g lidocaine and pH is adjusted with 1M HCl. The samples are not autoclaved.

| Poloxamers 188/407 (mg/g) | Cremophor EL (mg/g) | Co-solvent (mg/g) | pH | HCl tot (M) | Viscosity at 20° C. (Pa·s) | Rheology (dynamic oscillation) | Comments |
|---|---|---|---|---|---|---|---|
| | | | | | | 5000 Pa | gel at 50° C. |

Table 4 demonstrates a number of compositions useful within the specifications of the invention.

Example 5

Sterilization of the Compositions

Spores of *Geobacillus searothermophilus* (ATCC 7953) was added in different amounts to the composition (120 mg/g poloxamer 188, 90 mg/g poloxamer 407, 270 mg/g Cremophor EL, 50 mg/g lidocaine, water up to 1 g). 0.15 ml of spore suspension with different amount of spores in accordance with Table 5 were added to 30 ml product before autoclaving and incubation at 55-60° for 5 days.

TABLE 6

| Autoclave process | Amount of added spores (CFU/ml) | | | | |
|---|---|---|---|---|---|
| | $10^1$ | $10^2$ | $10^3$ | $10^4$ | $10^5$ |
| 110°/10 min | <5 | $1.1 \times 10^1$ | $2.5 \times 10^1$ | $3.7 \times 10^2$ | $2.3 \times 10^3$ |
| 115°/10 min | <5 | <5 | <5 | <5 | <5 |

The results indicate a sufficient sterility assurance level for lidocaine products according to the invention is obtainable at 115° C. for 10 minutes.

In order to assess how different autoclavation temperatures affected the stability of the product a composition including 110 mg/g poloxamer 188, 100 mg/g poloxamer 407, 270 mg/g Cremophor EL and 50 mg/g lidocaine was provided. The compositions were autoclaved at 121 and 115° C. for 10 minutes, respectively. Table 7 indicates that the level of impurities was significantly lower at 115° C.

TABLE 7

| Autoclave process | Impurity (% of lidocaine content) |
|---|---|
| 121°/10 min | 0.73 |
| 115°/10 min | 0.62 |

The invention claimed is:

1. A method of treating pain during an obstetric or gynaecological procedure which method comprises:
   (i) providing in a container a composition comprising:
      1 to 10% by weight of lidocaine in base form, said lidocaine being solubilized in 10 to 30% by weight of a polyoxyethylene castor oil,
      15 to 30% by weight of one or more non-ionic block copolymers of poly(oxyethylene) and poly(oxypropylene) type, and
      water,
      wherein the pH of the composition is at least the value of the pKa of said lidocaine; and
   (ii) applying said composition from said container to an internal mucosal surface of a patient in need of such pain treatment by intravaginal, intracervical, pericervical or intrauteral administration wherein the composition after said applying forms a thermogel on said mucosal surface.

2. The method according to claim 1 wherein said application is carried out during an obstetric procedure.

3. The method according to claim 2 wherein the obstetric procedure is labour.

4. The method according to claim 1 wherein said application is carried out during a gynaecological procedure.

5. The method according to claim 4 wherein the gynaecological procedure is an abortion, application of an intrauterine device, a hysteroscopy, in vitro fertilization or a general vaginal examination.

6. The method according to claim 1 wherein the composition further comprises an additional solubilizer in an amount of 1 to 5% by weight.

7. The method according to claim 6 wherein the additional solubilizer is a lower alcohol.

8. The method according to claim 6 wherein the additional solubilizer is selected from the group consisting of glycerol formal, glycofural, polysorbate 80, and ethyl acetate.

9. The method according to claim 1 wherein the amount of lidocaine is 1 to 7% by weight.

10. The method according to claim 1 wherein the amount of lidocaine is 3 to 5% by weight.

11. The method according to claim 1 wherein the polyoxyethylene castor oil is polyoxyethylene 35 castor oil.

12. The method according to claim 1 wherein the block copolymers comprise a higher molecular weight poloxamer and a lower molecular weight poloxamer, wherein the higher molecular weight poloxamer and the lower molecular weight poloxamer are present in about equal amounts.

13. The method according to claim 1 wherein the block copolymers are poloxamer 188 and poloxamer 407.

14. The method according to claim 1 wherein the composition has an elasticity modulus (G') below 20 Pa at room temperature and an elasticity modulus (G') in the range of 50 to 10000 Pa at body temperature.

15. A method of treating pain during an obstetric or gynaecological procedure which method consists essentially of:
   (i) application to a mucosal surface of a patient in need of such pain treatment of a composition comprising:
      1 to 10% by weight of lidocaine, said lidocaine being solubilized in 10 to 30% by weight of a polyoxyethylene castor oil,
      15 to 30% by weight of one or more non-ionic block copolymers of poly(oxyethylene) and poly(oxypropylene) type, and
      water,
      wherein the pH of the composition is at least the value of the pKa of lidocaine;
      wherein said application is carried out by intravaginal, intracervical, pericervical or intrauteral administration of said composition, and
   (ii) formation of a thermogel on said mucosal surface.

16. The method according to claim 15 wherein said application is carried out during an obstetric procedure.

17. The method according to claim 16 wherein the obstetric procedure is labour.

18. The method according to claim 15 wherein said application is carried out during a gynaecological procedure.

19. The method according to claim 18 wherein the gynaecological procedure is an abortion, application of an intrauterine device, a hysteroscopy, in vitro fertilization or a general vaginal examination.

20. The method according to claim 15 wherein the composition further comprises an additional solubilizer in an amount of 1 to 5% by weight.

21. The method according to claim 20 wherein the additional solubilizer is a lower alcohol.

22. The method according to claim 20 wherein the additional solubilizer is selected from the group consisting of glycerol formal, glycofural, polysorbate 80, and ethyl acetate.

23. The method according to claim 15 wherein the amount of lidocaine is 1 to 7% by weight.

24. The method according to claim 15 wherein the amount of lidocaine is 3 to 5% by weight.

25. The method according to claim 15 wherein the polyoxyethylene castor oil is polyoxyethylene 35 castor oil.

26. The method according to claim 15 wherein the block copolymers comprise a higher molecular weight poloxamer and a lower molecular weight poloxamer, wherein the higher molecular weight poloxamer and the lower molecular weight poloxamer are present in about equal amounts.

27. The method according to claim 15 wherein the block copolymers are poloxamer 188 and poloxamer 407.

28. The method according to claim 15 wherein the composition has an elasticity modulus (G') below 20 Pa at room temperature and an elasticity modulus (G') in the range of 50 to 10000 Pa at body temperature.

* * * * *